(12) United States Patent
La Valle Sansone et al.

(10) Patent No.: US 10,338,048 B2
(45) Date of Patent: Jul. 2, 2019

(54) FOOD FRESHNESS INDICATOR INK AND METHOD FOR THE MANUFACTURE OF A FOOD FRESHNESS INDICATOR INK

(71) Applicants: Chimigraf Ibérica, S.L., Rubí (ES); Instituto Tecnológico Del Embalaje, Transporte Y Logística (ITENE), Paterna (ES); Universidad Politécnica De Valencia, Valencia (ES)

(72) Inventors: Ugo La Valle Sansone, Rubí (ES); Antonio López Muñoz, Rubí (ES); Emilio Fernández García, Rubí (ES); Joaquín Cortiella Martorell, Rubí (ES); Núria Herranz Solana, Paterna (ES); Inmaculada Lorente Gómez, Paterna (ES); Maria Teresa Calvo Vilanova, Paterna (ES); Susana Aucejo Romero, Paterna (ES); Ramón Martínez Mañez, Valencia (ES); José Luis Vivancos Bono, Valencia (ES); Patricia Zaragoza Torres, Valencia (ES); José Vicente Ros Lis, Valencia (ES)

(73) Assignees: CHIMIGRAF IBÉRICA, S.L., Rubí (ES); INSTITUTO TECNOLOGICO DEL EMBALAJE, TRANSPORTE Y LOGÍSTICA (ITENE), Paterna (ES); UNIVERSIDAD POLITÉCNICA DE VALENCIA, Valencia (ES)

( * ) Notice: Subject to any disclaimer, the term of this patent is extended or adjusted under 35 U.S.C. 154(b) by 128 days.

(21) Appl. No.: 15/109,716

(22) PCT Filed: Jan. 9, 2015

(86) PCT No.: PCT/EP2015/050368
§ 371 (c)(1),
(2) Date: Jul. 5, 2016

(87) PCT Pub. No.: WO2015/104399
PCT Pub. Date: Jul. 16, 2015

(65) Prior Publication Data
US 2016/0327538 A1  Nov. 10, 2016

Related U.S. Application Data

(63) Continuation of application No. PCT/EP2015/050368, filed on Jan. 9, 2015.

(30) Foreign Application Priority Data

Jan. 10, 2014  (ES) ............... 20140030022

(51) Int. Cl.
*C09D 11/00* (2014.01)
*C09D 11/03* (2014.01)
*C09D 11/14* (2006.01)
*C09D 11/102* (2014.01)
*G01N 33/02* (2006.01)
*G01N 33/12* (2006.01)
*G01N 21/78* (2006.01)
*G01N 31/22* (2006.01)

(52) U.S. Cl.
CPC ............. *G01N 33/02* (2013.01); *G01N 21/78* (2013.01); *G01N 31/22* (2013.01); *G01N 33/12* (2013.01)

(58) Field of Classification Search
CPC ......... C09D 11/00; C09D 11/03; C09D 11/14; C09D 11/102; G01N 33/02; G01N 33/12; G01N 21/78; G01N 21/22
USPC ..... 106/31.03, 31.14, 31.24, 31.64; 426/231, 426/232, 87; 422/86, 400; 436/1, 21, 436/164; 116/206
See application file for complete search history.

(56) References Cited

U.S. PATENT DOCUMENTS

| | | | | |
|---|---|---|---|---|
| 4,019,865 A | * | 4/1977 | Sinclair | G01N 31/224 116/206 |
| 4,328,181 A | * | 5/1982 | Anders | G01N 31/224 116/206 |
| 4,746,616 A | * | 5/1988 | Honigs | G01N 31/22 116/206 |
| 5,407,829 A | * | 4/1995 | Wolfbeis | G01N 31/22 422/400 |
| 6,149,952 A | * | 11/2000 | Horan | G01N 31/223 426/87 |
| 6,495,368 B1 | * | 12/2002 | Wallach | G01N 31/221 436/164 |
| 6,686,308 B2 | | 2/2004 | Mao et al. | |
| 7,153,532 B1 | | 12/2006 | Elsome et al. | |
| 7,785,894 B2 | * | 8/2010 | Smolander | G01N 31/223 116/206 |

(Continued)

FOREIGN PATENT DOCUMENTS

DE  19605522 A1  8/1997
EP  0 449 798 A2  10/1991

(Continued)

OTHER PUBLICATIONS

International Search Report and Written Opinion from Corresponding Application No. PCT/EP2015/050368; dated Mar. 23, 2015.

(Continued)

*Primary Examiner* — Helene Klemanski
(74) *Attorney, Agent, or Firm* — Pearne & Gordon LLP

(57) ABSTRACT

Food freshness indicator ink and method for the manufacture of a food freshness indicator ink. It comprises a varnish that constitutes between 90-98% of the total, the varnish comprising between 5-25% of the total amount of the varnish of at least one film-forming resin or at least one vinylic resin or a mixture thereof, between 10-25% of the amount of the resin of a plasticizer additive and between 50-75% of the total amount of the varnish of solvents, and between 2-10% of the total of metallic salts.

15 Claims, 4 Drawing Sheets

(56) References Cited

U.S. PATENT DOCUMENTS

| | | | |
|---|---|---|---|
| 2005/0112085 A1* | 5/2005 | MacDonald | G01N 31/22 424/76.1 |
| 2006/0057022 A1 | 3/2006 | Williams et al. | |
| 2009/0137054 A1 | 5/2009 | Hoagland et al. | |

FOREIGN PATENT DOCUMENTS

| | | |
|---|---|---|
| JP | 61-287972 A | 12/1986 |
| JP | 09-288076 A | 11/1997 |
| JP | 2001-208746 A | 8/2001 |
| JP | 2002-523777 A | 7/2002 |
| JP | 2004-108929 A | 4/2004 |
| JP | 2007-508105 A | 4/2007 |
| WO | 00/13009 A1 | 3/2000 |
| WO | 2005/039656 A1 | 5/2005 |
| WO | 2009/058891 A2 | 5/2009 |
| WO | 2009/070760 A1 | 6/2009 |
| WO | 2011/045572 A1 | 4/2011 |

OTHER PUBLICATIONS

International Preliminary Report on Patentability from Corresponding Application No. PCT/EP2015/050368; dated Jan. 14, 2016.
Chinese Office Action dated Jan. 9, 2018 from Corresponding Chinese Application No. 201580004272.1 (with English translation).
Notification of Reasons for Refusal in corresponding application JP 2016544554, dated Oct. 30, 2018.

* cited by examiner

FOOD FRESHNESS INDICATOR INK AND METHOD FOR THE MANUFACTURE OF A FOOD FRESHNESS INDICATOR INK

The present invention is an improvement in the field of inks that change colour with the degradation or decrease in food freshness and methods for the manufacture thereof.

BACKGROUND ART

At present, quality and safety are key priorities for the food industry and the authorities, and that is why the current lines of research in Europe are focused specifically to ensure the quality and safety of food.

Obviously, the packing and packaging systems containing and protecting food during all their shelf life are also subject to this trend. In particular, the primary packaging, which is a vital element in ensuring the quality and safety of the packaged product, plays a crucial role in attaining this goal.

Furthermore, it has been found that the amount of discarded products along the supply chain, which could actually be consumed without problems, is worryingly high.

The availability of a system that reports in an individual, non-destructive way and in real-time the quality and safety of food is a complementary and valuable tool for achieving the objectives established by the European Union.

At present, the expiration date is set according to the date of production, so the first thing that is produced is the first thing that should be consumed, regardless of the storage conditions or the initial microbial load of the product, which sometimes causes the product to be discarded when it could really be consumed in perfect condition, or that poisonings occur through the consumption of a spoiled product.

In the prior art different inks are known that change colour with the change of the food's condition.

Thus, the German Patent No. 19605522, year 1996, in the name of KARLSRUHE FORSCHZENT which belongs to the state of the art, refers to a layer that is sensitive to an opto-chemical sensor having a metal complex of phthalocyanine fixed in a porous matrix.

European Patent No. 0449798 in the name of AVL MEDICAL INSTRUMENTS, year 1991, is also known, which refers to a method for quality control of packaged organic substances, preferably packaged food products, tea, coffee, tobacco and medicines, wherein the substances to be examined are brought into contact with a planar optical sensor element which is mounted inside the packaging and reacts to the change in the gas composition in the space above the sample through a change in colour or fluorescence. The change in one of the optical properties of the sensor element is detected visually or optoelectronically.

There are other patents which may be considered, such as US2006057022 "FOOD QUALITY INDICATOR", year 2005, which refers to an indicator that uses natural pH indicators and reacts to acids such as $H_2S$. It is an indicator that cannot be used in a modified atmosphere.

Within the same group is Patent WO2011045572 "INTELLIGENT PIGMENTS AND PLASTICS", year 2010, which refers to an indicator such as a melted processed polymer composite for use in food packaging, which is sensitive to $CO_2$, $O_2$ and $NH_3$, with indicators such as m-cresol purple, bromophenol blue, methylene blue, etc., being said dye or ink for coating or impregnating with inorganic pigments such as, $SiO_2TiO_2$, $Al_2O_3$, MgO, zeolites, which results, in the end, in a water soluble ink. As it uses $CO_2$, it cannot be used in a modified atmosphere.

Thus, Patent WO2009/070760 "HYDROGEN SULFIDE INDICATING PIGMENTS", year 2008, refers to pigments that react to hydrogen sulphide, with application to environmental security. It is known that metals react to hydrogen sulphide by changing their colour; however, the colour change does not occur gradually nor is directly linked to the concentration of deteriorating compounds of food in controlled atmospheres inside the fresh product packaging.

U.S. Pat. No. 7,153,532, in the name of Johnson Matthey PLC, year 2001, is an antecedent which refers to a sensor for detecting food spoilage or the opening or rupture of the package comprising a metal complex fixed at or on a substrate, which complex is capable of releasing a detectable component.

Given this situation, and in order to ensure the quality and safety of food and decrease the amount of food wasted, it is of interest to provide tools and methods which provide information on the shelf life of food in real time, based on specific aspects of the product, such as for example, microbial load or physical and chemical characteristics, and not on the currently used estimation methods.

The closest document is the cited U.S. Pat. No. 7,153,532. This document primarily addresses the detection of the grade of freshness in packaged foods by an ink composition comprising indicator compounds, resins, solvents and additives. Thus, the change in the optical properties is undergone by the chromophores and/or fluorophores joined to the metal centre, showing a colour change and a change in fluorescence when the product is inedible. In addition, some of the elements used such as titanium or rare earths are not very suitable for the packaging of low cost food, since their cost does not compensate the economic cost of the product. Finally, the referred to document has the following limitations:

it requires an optical element for viewing, and
the indicator developed has included a metal complex whose manufacturing process on an industrial scale is not defined or optimized.

SUMMARY OF THE INVENTION

The object of the present invention is a food freshness indicator ink, in particular for those foods that, in their process of degradation, emit sulphured compounds such as hydrogen sulphide, dimethyl sulphide, dimethyl disulphide, 2,3-dimethyl trisulphide, thiols such as methanethiol, ethanethiol, methylmercaptane or similar, characterised in that it comprises: between 90-98% of the total of a varnish, and between 2-10% of the total of metallic salts. Wherein said varnish comprises between 5-25% of the total amount of the varnish of at least one film-forming resin or at least one vinyl resin or a mixture thereof, between 10-25% of the amount of the resin of a plasticiser additive and between 50-75% of the total amount of the varnish of solvents.

A further object of the invention is a method for manufacturing a food freshness indicator ink, particularly for foods that, in the degradation process, emit sulphured compounds such as hydrogen sulphide, dimethyl sulphide, dimethyl disulphide, 2,3-dimethyl trisulphide, thiols such as methanethiol, ethanethiol, methylmercaptane or similar, of the type characterized by comprising: a first phase in which a varnish is prepared by adding at least one vinylic resin or at least one film-forming resin or a mixture thereof, with at least one plasticizer additive, which is compatible with the resin, wherein all components are added to a solvent mixture and stirred until complete solubility, wherein the content of resin is between 5-25% of the total, wherein the content of plasticizer additive is between 10-25% of the amount of resin and the content of solvents is between 50-75% of the total, a second phase in which a concentrated base ink formed by the varnish obtained by adding the product of the previous phase and a metal salt is prepared, said metal salt (indicator) being slowly stirred into the varnish, subsequently stirring all components and defining a concentrated base ink, wherein the content of the metal salts is 15-30% and the content of varnish is between 70-85% of the total amount of the ink, a third phase in which the dispersion of the previous phase product is ground in a bead mill to obtain a dispersion of even particle-size distribution smaller than 5μ, and a fourth phase in which this concentrated base ink is diluted in the varnish produced in the first phase, to a metal salt concentration between 2 to 10% of the total weight of the ink.

The food freshness indicator ink of the present invention may be immobilised in a porous support or a polymeric matrix, such as a film, be incorporated into, or into part of, a packaging material. Thus, an additional object of the present invention is a label comprising the food freshness indicator ink as defined herein for detecting gaseous substances comprising sulphur-containing compounds and formed by microbial food spoilage. The label is formed by printing the food freshness indicator ink on a film or a porous substrate. A food package comprising the label is also an object of the invention.

BRIEF DESCRIPTION OF THE DRAWINGS

To facilitate the explanation, three sheets of drawings are attached in which a practical case of the embodiment, which is cited as an example, not limiting the scope of the present invention, is shown.

DETAILED DESCRIPTION OF THE INVENTION

Figure 1:
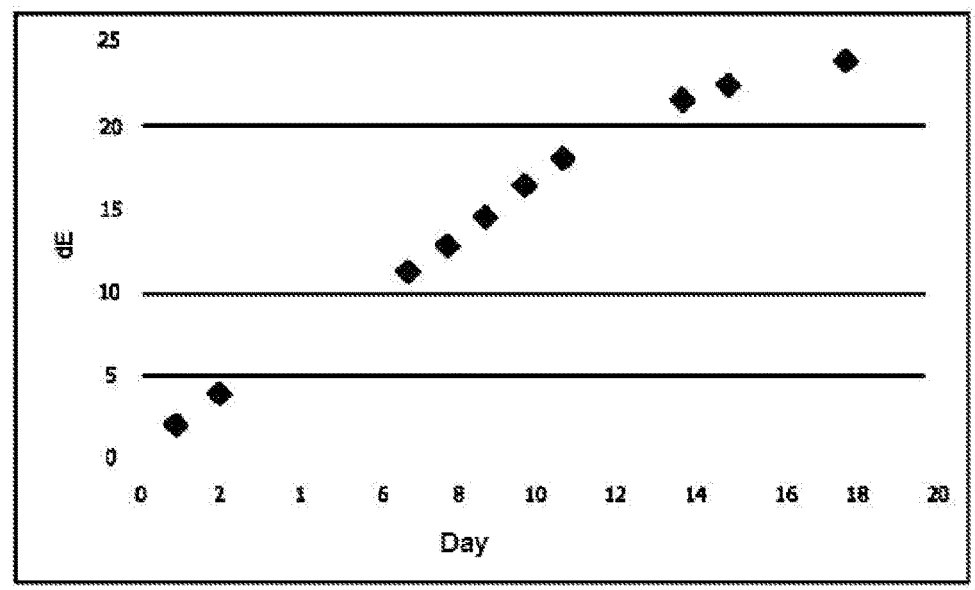
FIG. 1 is a graph of the mean colour differences of indicators evaluated to time and compared to their initial colour.

The present invention is an improvement over the prior art as the ink obtained in the process does not require optical elements for viewing (fluorescence change), so that anyone, with the naked eye, can see the degree of freshness of the food being sold, in addition, the colour change is experienced by the metal itself without the need of forming complexes with photoactive groups, it is much more accurate in the colour change as it is fully consistent with the food spoilage and obtained more economically. Additional advantages are also derivable from the objects and embodiments of the present invention, among others:

All materials used in the manufacture of the indicator are suitable for food contact or are also known as "food contact", because they are verified on the positive lists and legislation of materials suitable for food contact.

In addition, the materials used are inexpensive materials, so that the cost of development can be assumed by low-priced food products.

An irreversible change: if the package is broken and the gas composition inside is modified, the indicator does not revert to its original colour, so it will not show a false negative.

Meat freshness and safety accuracy: The indicator colour development is exactly related with the meat freshness and safety.

Individual control: all items can be controlled, through the whole supply chain, from manufactures to consumer. Current quality controls analyze only some items of a batch because the tests are destructive. This solution shows on time information of each product in a non-destructive way.

Eco-friendly solution: it is produced as common pressure sensitive labels sticked on meat trays, so its use will not imply additional environmental impacts.

Stable colour: the label colour development is only due to metabolites presence, consequently due to the quality and safety of the product.

Gradual colour change. The gradual colour change measured by Cie-lab coordinates, represents the different stages of freshness and is correlated with the following qualitative and quantitative parameters:
  Organoleptic state of the food (not contemplated in the indicator described in the art)
  Microbiological state of the food
  Concentration of sulfur compounds in the headspace as a consequence of food spoilage.

All this makes the present invention suitable for the packaging of food products, which in the degradation process emit sulphur-containing compounds.

Thus, in a particular embodiment, the method for manufacturing a food freshness indicator ink for fresh food such as fish, poultry, pork or beef, which in the process of degradation emit sulphured compounds such as hydrogen sulphide, dimethyl sulphide, dimethyl disulphide, 2,3-dimethyl trisulphide, thiols such as methanethiol, ethanethiol, methylmercaptane, etc., comprises the following phases:

A first phase in which a varnish is prepared by adding a cellulose derived resin or a mixture thereof, such as ethylcellulose, cellulose aceto-propionate, nitrocellulose, and vinylic resins and other similar film-forming resins. In this embodiment, a nitrocellulose wetted in alcohol is used, such as for example nitrocellulose (N content <12.3%) 65% by weight wetted in isopropyl alcohol of ¼ viscosity that presents good solubility in a blend of ethyl alcohol and ethyl acetate, althouth other cellulose derived resins such as ethylcellulose, cellulose aceto-propionate, etc., are also conceivable.

The above resin is plasticized with at least one compatible plasticiser additive with cellulose derived resin. In this embodiment acetyl tributyl citrate is used. Plasticisation is performed because the cellulose derived resin, when printed, forms films that are stiff and brittle, hence plasticising with acetyl tributyl citrate gives it greater flexibility.

The resulting mixture is added to a solvent mixture and stirred until complete solubility at 600 rpm. Depending on the printing process (flexography, gravure, inkjet, . . . ) the formulation will be produced with the most suitable solvents (ethyl alcohol, ethyl acetate, n-propyl acetate, n-propyl alcohol, methoxy propanol, ethoxy propanol, . . . or mixtures thereof), taking into account factors such as the solubility of the resin, the evaporation rate, the tendency to be retained in the carrier, no or low noxiousness, etc.

In accordance with the present invention, the viscosity of the varnish measured in Ford Cup No. 4 (FC/4) is comprised between 10"-50" at 20° C., preferably between 15"-45", more preferably between 25"-40" at 20° C.

So a base composition would be formed by a content of the cellulose derived resin between 5-25% of the total, a content of the plasticizer additive between 10-25% of the amount of resin and a content of solvents between 50-75% of the total, which is summarised in the following example:

Nitrocellulose (65% solids): 20%
Acetyl tributyl citrate: 5%
Ethyl alcohol 99.8°: 60%
Ethyl acetate: 15%

The viscosity of the varnish measured in Ford Cup No. 4 (FC/4) is 25"-40" at 20° C.

Then in the second phase, wherein a concentrated base ink formed from the varnish obtained in the previous step and a metal salt is prepared.

The metallic salts (indicator) may be, for example, copper salts or iron salts, in particular copper carbonate and iron nitrate.

The metal salt (indicator) is incorporated by adding it in slow stirring to the varnish, and all subsequently stirred at, for example, 1200 rpm for 15 minutes, defining a concentrated base ink, the content of metal salts being between 2-10% of the total ink and the content of varnish between 90-98%.

An example of formulation could be:
Copper salt: 10%
Varnish: 90%

In the third phase in which the dispersion of the previous phase is milled with microspheres, for example of zirconium/yttrium oxide between 0.6 mm-1.2 mm in diameter, until a uniform dispersion of particle-size distribution smaller than 5μ is obtained.

It is subjected to recirculation for at least 30 min in the bead mill. A dispersion of uniform particle-size distribution of a pale bluish-green colour (in case of copper salt) and dark brown (in the case of the iron salt) is obtained. The viscosity of the base ink measured in Ford Cup No. 4 (FC/4) is 25"-50" at 20° C.

Finally, in the fourth phase, the concentrated base ink obtained in the third phase is diluted with the varnish made in the first phase, to a metal salt concentration between 2 and 10% of the total weight of the ink.

Thus, the indicator ink for the freshness of poultry object of the present invention comprises:

| Varnish | 90-98% |
|---|---|
| Metallic salts | 2-10% |

The varnish, in turn, comprises:
a content of cellulose derived resin of 5-20% of the total amount of the varnish,
a content of plasticizer additive of 10 to 25% of the amount of resin, and
a content of solvents of 50-75% of the total of varnish.

In this embodiment, a nitrocellulose wetted in alcohol or in another solvent compatible with the formulation is used, such as for example 65% by weight of nitrocellulose (content N<12.3%) wetted in isopropyl alcohol of ¼ viscosity that presents good solubility in a blend of ethyl alcohol and ethyl acetate, although other cellulose derived resins such as ethyl cellulose, aceto-propionate cellulose, vinyl resins and other similar film-forming resins are also conceivable.

The plasticising additive must be compatible with the cellulose derived resin. In this embodiment acetyl tributyl citrate is used. Plasticisation is performed because the nitrocellulose, when printed, forms films that are stiff and brittle; hence it is plasticised with acetyl tributyl citrate to give it greater flexibility.

Depending on the printing process (flexography, gravure, inkjet, . . . ) the formulation will be developed with the most suitable solvents, taking into account factors such as the solubility of the resin, the evaporation rate, the tendency to be retained in the carrier, no or low noxiousness, etc.

An example of varnish is as follows:
Nitrocellulose (65% solids): 20%
Acetyl tributyl citrate: 5%
Ethyl alcohol 99.8°: 60%
Ethyl acetate: 15%

The percentages are by weight based of the total to which they refer.

The viscosity of the varnish measured in Ford Cup No. 4 (FC/4) is 25"-40" at 20° C.

With respect to the metal salts, they may be copper or iron, for example.

This is an indicator ink containing an indicator compound in its formulation, i.e. metallic salt. Once the indicator ink is manufactured by the method explained above, it is printed on a porous substrate such as paper and cardboard of different qualities, suitable for food contact and permeable to the volatile compounds but impermeable to the passage of the ink components to the product packaged, then a strip is printed with the reference colours indicating the state of degradation. This printed strip is self adhesive to stick on the inner face of the packaging, for example on the inner face of the sealing films of trays containing the product.

Food is degraded by various processes: physical, chemical, biological, environmental, etc. In the case of packaged food, degradation by physical processes (such as knocks) is minimal and degradation is mainly due to the growth of microorganisms, which is enhanced if environmental conditions (temperatures) are not adequate. During the shelf life of foods, these organisms grow and multiply at the expense of the product itself, modifying their sensory characteristics and generating volatile compounds, such as volatile sulphured compounds, which accumulate in the head space of the container. The lower the shelf life of the food, the higher is the concentration of volatile compounds in the head space of the container. These compounds cross the porous substrate on which the indicator ink is applied, reacting with the metallic salt and causing a change in colouration.

This change is proportional to the concentration of volatile sulphured compounds in the head space of the container, and therefore correlates with the shelf life of the packaged product. This indicator also has a printed legend that explains what shelf life corresponds to each colour of the indicator ink, so that the consumer, when using it, has no doubts about the information displayed on the indicator.

Printing methods are traditional printing systems (flexography, gravure, inkjet . . . ) used in printing labels and known to those skilled in the art. Finally, all the print is protected with a carrier material (e.g. silicone release paper). To use the indicator ink in the indicator, the described freshness indicator ink is printed on a porous substrate that is permeable to the volatile compounds.

The printing process used can be flexography, gravure, inkjet, etc., to give a dry film thickness between 0.05 and 3 microns. Subsequently the indicator legend is printed with all information necessary for the interpretation of the indicator colour. Next, an adhesive layer is printed and the printing is protected with a carrier material (e.g. silicone release paper).

This indicator is stuck to the inner surface of the sealing film containing a tray-packaged meat such as poultry in a modified atmosphere of, for example, 70% $CO_2$ and 30% $N_2$. The tray with the indicator is stored at a refrigeration temperature of 4° C.

After conducting sensory and microbiological analyses (visual and olfactory assessment evaluation) (total aerobes, Enterobacteriaceae and *Salmonella*), it is determined that the product reaches the end of its shelf life between 9 and 15 days after packaging.

In one example in which a shelf life of 9 days was obtained, the average colour of the indicator on packaging day 0 is L=91.8; a=−2.44; b=5.91. The average colouring of the indicator on 9 packaging day is L=78.80; a=0.99; b=11.32. The average colouring difference between the indicator initial colour and final colour is 14.5 (FIG. 1). As shown in FIG. 1, the colour change occurs gradually, according to food spoilage.

In a merely illustrative and exemplary way, four figures explaining in a more visual way changes that users might observe depending on the food shelf life are attached.

Figure 2:
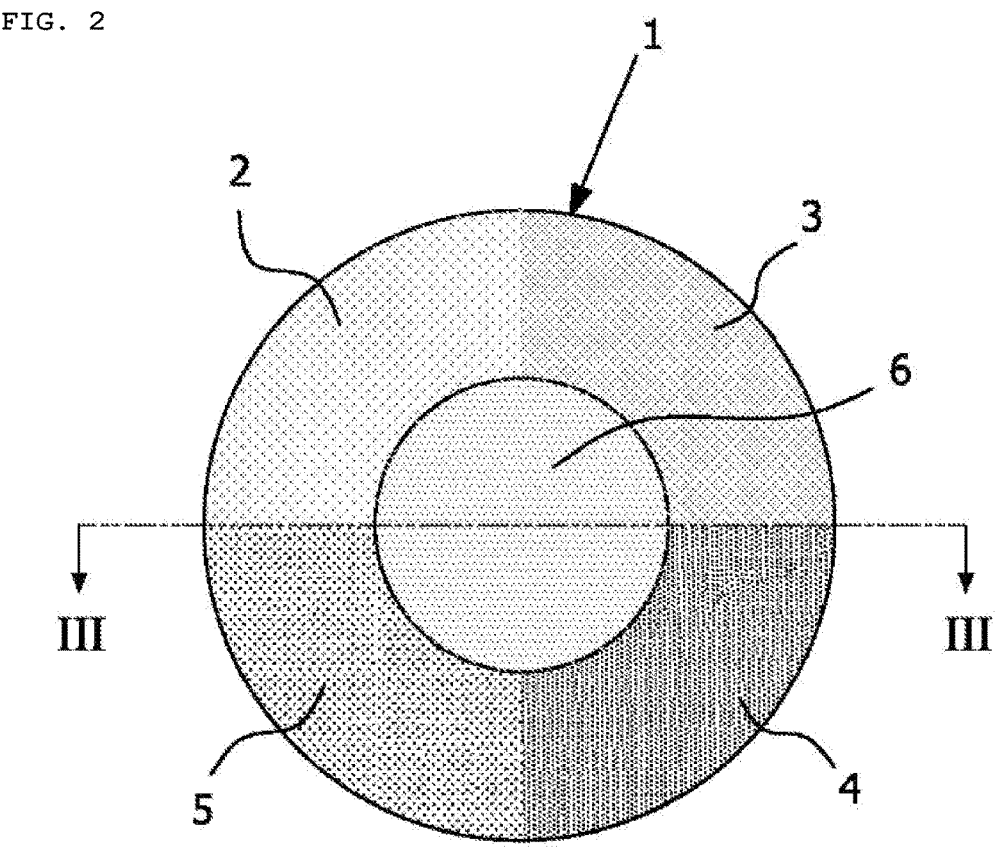
FIGS. 2 and 4 are two possible designs that the indicator can present.
Figure 4:
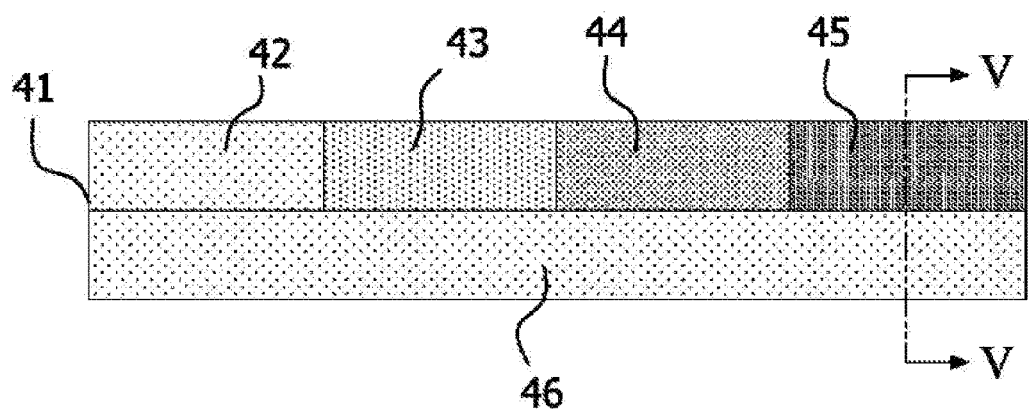

FIGS. 2 and 4 are two possible designs that the indicator can present. The one in FIG. 2 is a disc-shaped design (1, while that in FIG. 4 is a strip-shaped design (41), which are to be attached, for example, inside the packaging, on the film thereof.

Both the disc (1) as the strip (41) are divided into four cells, of which (2,3,4,5) for the disc and (42,43,44,45) for the strip, defining a colour depending on the degradation of the food and the emission of sulphured compounds, wherein the ink permeates the porous substrate (6,46).

Other possible designs that the indicator may present are disc or strip shaped divided into 2, 3 or 5 cells, each defining a colour depending on the degradation of the food and the emission of sulphured compounds.

Thus, if the food has a shelf life of 1-3 days, the colour would be like the one in cells (2,42), in case of a shelf life of 4 to 7 days, it would change its colour to that of cells (3,43), in case it reaches a shelf life of more than one week, its colour would be that of cells (4,44), and finally, if its consumption were no longer advisable due to its degraded condition, its colour would be that of the last cell (5,45).

Figure 3:
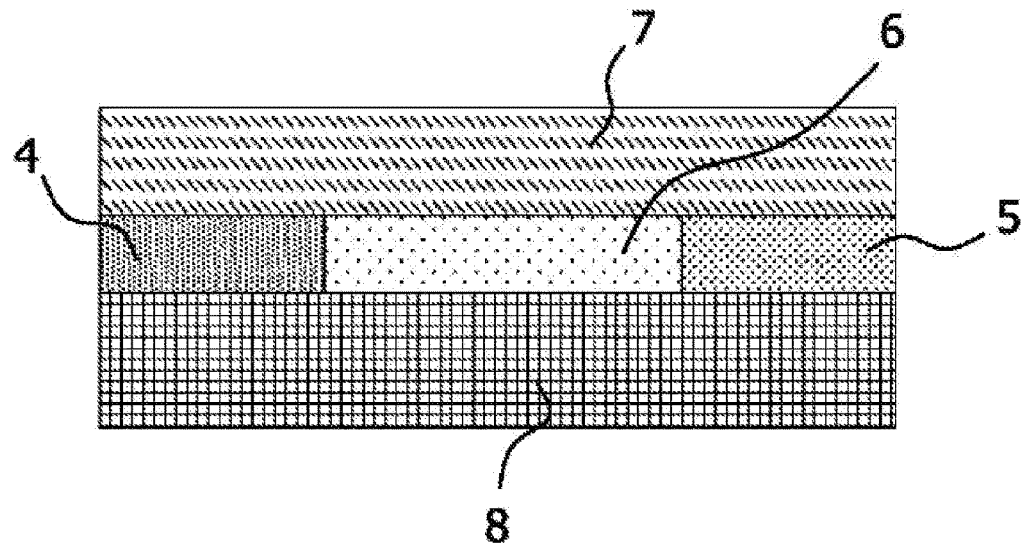
FIGS. 3 and 5 are profile views of FIGS. 2 and 4 and show the structure of the indicator.
Figure 5:
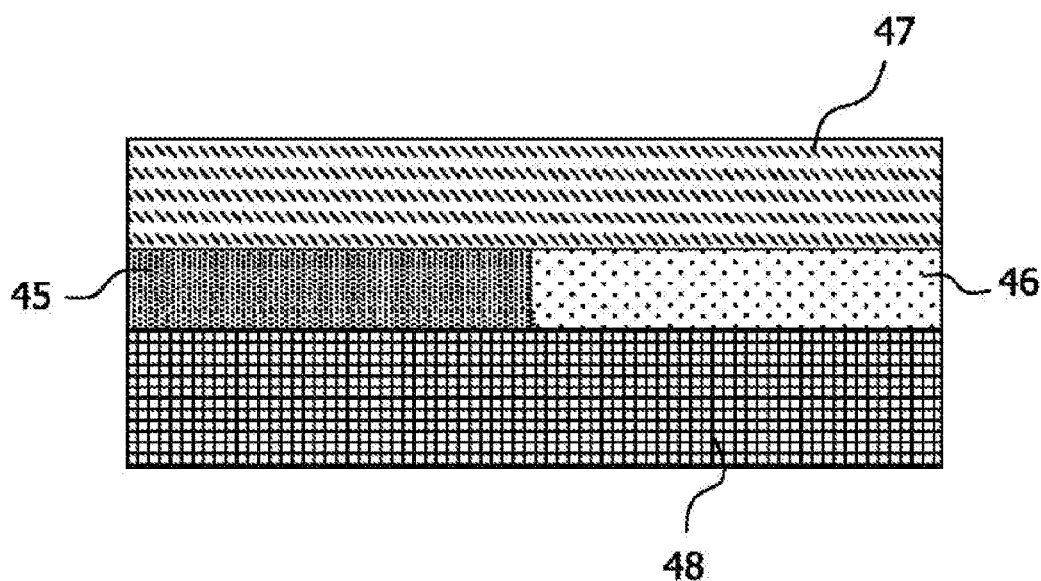

In FIGS. 3 and 5, which are sections of FIGS. 2 and 4 and show the structure of the indicator, both the placement of the indicator ink (8,48) and the transparent adhesive (7,47) can also be seen.

The present invention discloses a new food freshness indicator ink and a method for the manufacture of a food freshness indicator ink.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

Food freshness indicator ink was prepared according to the process as defined above. Following composition was obtained:
Copper carbonate 9%
Nitrocellulose 6%
Acetyl tributyl citrate 3%
Ethyl acetate 14%
Flexographic printing process was the printing technique used.

The label was made by a paper (FOOS GLOSS) and adhesive (FOOD GRADE). The metabolite has to pass through the paper and adhesive (FOOD GRADE) in order to contact with the indicator label. For this reason the final colour of the label at the end of chicken shelf life is grey.
Label and Ink Characteristics:
Label Surface printed: 10×20 cm.
Density 0.873 $g/m^3$.
Anilox used, has a theoretical deposition of 15 $cm^3/m^2$.
The indicator ink, final content in the label:
0.5 microns of thickness.
1.3095 10−5 $g/m^2$.
2.619 10−7 g/label (10×20 cm: label Surface printed).

Chicken breast pieces were purchased in a local slaughterhouse. Chicken breast were packaged (SMART 300 Traysealer; ULMA, Spain) in PP/EVOH/PP trays, and a barrier PP/PA film was used as a sealing top. The ratio between the volume of gas and weight of food product (G/P ratio) was 3.5:1 (v/w). Chicken was packaged using 70% N2-30% CO2 of MAP conditions. A headspace gas analyser (PBI Dansensor Check Mate II; Denmark) was used to adjust MAP composition during packaging of chicken breast. The indicators with applied freshness ink were adhered in the inner layer of PP/PA film of each packaged tray with an adhesive tape. Samples were stored in a refrigerator at two different constant temperature conditions: 4° C. and 15° C. 10 replicates for each temperature with indicators A, B and C were studied.
Headspace Measure.

It is known that packaged chicken breast under modified atmosphere emit mainly $H_2S$ and dimethyl sulphide as a consequence of its bacterial spoilage.

In order to determine the maximum concentration of those sulphur containing compounds at the headspace, measured at different days after packaging, a gases-mass cromatograph equipped with two specific columns for sulphureted compounds determination (PPQ and 5A) was used.

Table 1 shows the results obtained:

TABLE 1

| Sample | $O_2$ (%) | $N_2$ (%) | $CO_2$ (%) | $CH_4$ (ppm) | $H_2$ (%) | $H_2S$ (ppm) |
|---|---|---|---|---|---|---|
| 1 day expired | 12 | 47 | 34 | 82 | 0.84 | 715 |
| 2 days after packaging | 43 | 6 | 50 | 20 | 0.06 | <50 |

TABLE 1-continued

| Sample | $O_2$ (%) | $N_2$ (%) | $CO_2$ (%) | $CH_4$ (ppm) | $H_2$ (%) | $H_2S$ (ppm) |
|---|---|---|---|---|---|---|
| 7 days after packaging | 23 | 17 | 63 | 19 | — | <50 |

Sensory Analysis

Quantitative descriptive analysis was used to assess breast chicken inside the trays on different post-packaging days. Odour, colour, visual aspect and lixiviated liquids were the attributes used by a trained sensory panel (5 evaluators) to conclude a global score of each sample as a sensory quality quantification versus a standard (packaged fresh sample). The acceptability limit was the score 5 with 3 corresponding to an unacceptable quality (clearly recognizable off-odour and inedible). The samples were tempered during 15 minutes at 25° C. Furthermore, batches were assessed for colour before opening pouches and for odour just after opening them. A minimum of three samples were evaluated.

Thus, evaluators were asked to indicate in a non-structured lineal scale the difference of intensity of the different attributes. Lower the distance, higher the difference with the standard.

Figure 6:
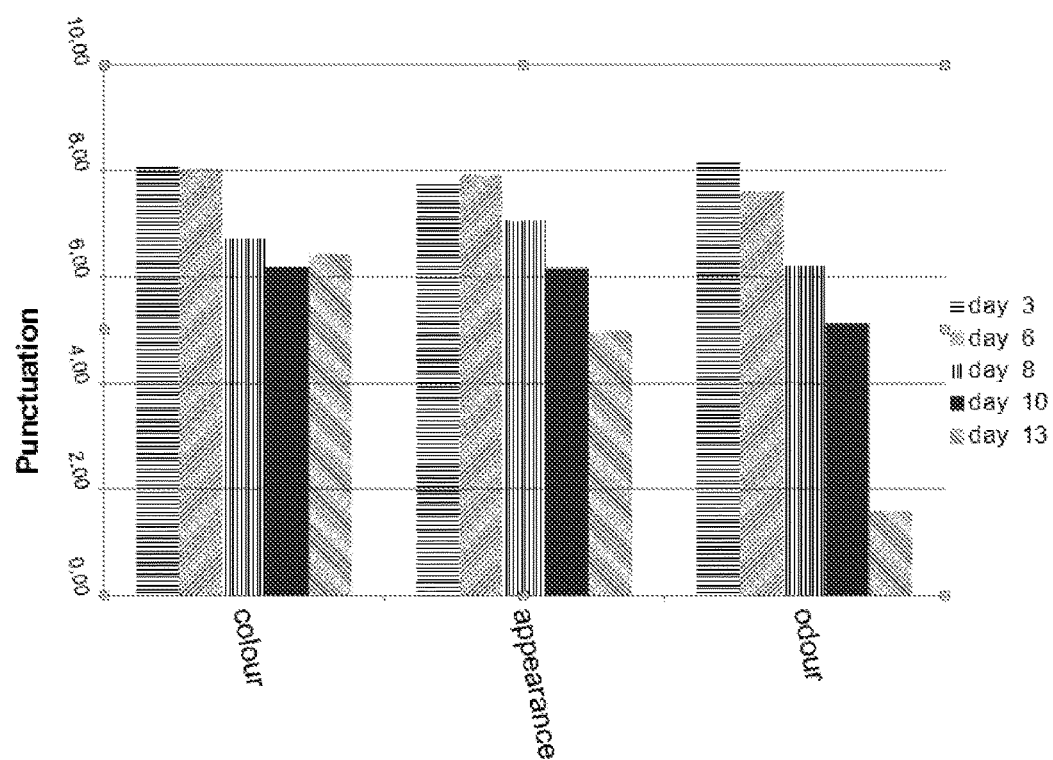
FIG. 6 shows the results of the sensory analysis.

FIG. 6 shows the results of the analysis.

Results show that the main attribute which relates to the quality of the packaged food is the odour.

Product colour hardly differentiates from the control sample throughout the experiment. By contrast, the general appearance of the product itself that would deteriorate throughout the trial and only the last day he received a less than 5 score of 10. Regarding the smell parameter, it achieved a rating of 5 out of 10 on day 10.

Microbiological Analysis

Regarding microbiological analysis as a complementary test with sensory analysis for study chicken shelf life, aerobic plate counts, enterobacteriaceae and *salmonella* considering legal limits, were studied:

Legal Limits:
Aerobic plate counts ($10^6$ UFC/g)
Enterobacteriaceae ($10^2$ UFC/g)
*Salmonella* (no presence)

Chicken breast samples were removed from the pouches using sterile scalpels and forceps. Two cores of 10±0.1 g, were aseptically removed from each sample and blended with a 90 ml of 1% peptone water (w/v) for 60 s in a Stomacher (BagMixer 400; Interscience, France). Additional dilutions were made in 1% peptone (w/v). Then 1 ml of the undiluted homogenate and of each dilution was spread on duplicate plates. Bacterial numbers were determined form plates bearing 30-300 colonies. Counts were obtained as follows: Aerobic plate counts on Plate Count Agar (Scharlab®), incubated at 32° C. for 48 h; Enterobacteriaceae on Violet Red Bile Glucose Agar (Scharlab®), incubated at 37° C. for 24 h and *Salmonella* on *Salmonella Shigella* Agar (Scharlab®), incubated at 37° C. for 24 h. A minimum of three samples were evaluated.

In terms of microbiological quality, aerobic plate counts exceeded legal limit ($10^6$ UFC/g) also at different times according to temperature storage conditions. 15° C. batch lingered up to day 2 and 4° C. batch with a slower evolution, reached legal limit in post-packaging day 18.

Enterobacteriaceae count showed the same result as aerobic plate counts and only in post-packaging day 18 for 4° C. batch there was presence of *Salmonella*.

As a conclusion, in order to obtain a unified parameter of chicken breasts shelf life for comparing the colour change evolution of freshness indicators, according each temperature, an inferred value of shelf life was assumed regarding sensory and microbiological analysis. For each batch, microbiological results were considered prevalent due to its higher objectivity than sensory panel. As Table 2 shows, post-packaging day 2 and for 15° C. and 4° C. batch respectively, were the end of shelf life for analyzed packaged chicken breasts.

TABLE 2

Chicken meat shelf life study

| Analysis | Shelf life 15° C. batch (post packaging days) | Shelf life 4° C. batch (post packaging days) |
|---|---|---|
| Sensory | 1-2 | 15 |
| Microbiological | 2 | 18 |
| Inferred shelf life | 2 | 18 |

Colour Measurement

CIELab coordinates (L*, b* a* values) of freshness indicators applied in each chicken breast packaging were measured using a spectrophotometer (Konica Minolta, model cm-2500d). A circular measurement area (D=8 mm) and a calibration with a white standard plate (L=100) was used. ΔE in order to evaluate colour change of tested indicators was calculated according to formula I:

$$\Delta E = \sqrt{(L_{initial} - L)^2 + (a_{initial} - a)^2 + (b_{initial} - b)^2}$$

Data treatment was carried out with SpectraMagic NX software to obtain pseudo-colour of each indicator.

The experiments were carried out in vials:

The reaction taken into account was the following:

$$Na_2S + 2HCl \rightarrow H_2S + 2NaCl$$

Labels with the food freshness indicator ink printed thereon were placed in the top of the vials in the headspace, taped to the wall thereof.

Several vials were filled with 2 ml of water and closed.

In a vial, the required amounts of $Na_2S$ and water to give a concentration of 10,000 ppm of $H_2S$ in a total volume of 2 ml were placed; was sealed and concentrated HCl was added. Stoichiometric amounts of both substances ($Na_2S$ and HCl) were considered.

From this stock solution dilutions are made taking a suitable headspace volume and taking it to a previously prepared vial with 2 ml of water (the headspace of the vial was 18 ml).

The amount taken depends on the concentration at which you want to reach.

Then the concentrations considered to carry out the correlation between the concentrations and the color change of the label, using water and without water, in order to determine their influence, since in the real packaging of chicken breasts with modified atmosphere there is moisture:

To Empty Vials:

1) 2 ml from a mother dissolution of 7952.92 ppm in a 20 ml vial.
2) From the headspace 1.5 ml, 1 ml and 0.5 ml were taken and brought to 20 ml vials (empty); concentrations were 596.47, 397.65 and 198.82 ppm respectively.
3) From the solution containing 596.47 ppm, 2 ml were taken and brought to a 20 ml vial, the final concentration was 59.65 ppm.

To the vials containing a volume of 2 ml water:

4) 2 ml from a mother dissolution containing 10,000 ppm in a 20 ml vial.
5) From the headspace 1.5 ml, 1 ml, 0.5 ml were taken and brought to 20 ml vials (with a volume of 2 ml water and 18 ml headspace); concentrations were 833.33, 555.56 and 277.78 ppm respectively.
6) From the solution containing 833.33 ppm, 2 ml were taken and brought to a 20 ml vial (with 2 mL of water), the final concentration was 92.59 ppm.

Table 3 resume the $H_2S$ concentrations generated in the vials with and without water

TABLE 3

| Empty Vials ($H_2S$ 20 ml) | | Vials with 2 ml water ($H_2S$ 18 ml) | |
|---|---|---|---|
| Disolution/vial | Concentration (ppm) | Disolution/vial | Concentration (ppm) |
| 1 (Mother) | 7952.92 | 4 (Mother) | 10.000 |
| 2 (1) | 596.47 | 5 (1) | 833.33 |
| 2 (2) | 397.65 | 5 (2) | 555.56 |
| 2 (3) | 198.82 | 5 (3) | 277.78 |
| 3 | 59.65 | 6 | 92.59 |

Labels with printed indicator ink changed colour in a range of very short time. Then, we proceed to quantify the shift thereof using a spectrophotometer, which quantify the color with Cie-Lab coordinates.

Table 4 shows the data resulting from the measurement of Cie-Lab coordinates of labels that have changed their colour.

TABLE 4

| | | Cie-Lab | | | | | | | | | | |
|---|---|---|---|---|---|---|---|---|---|---|---|---|
| | | L*(D65) | a*(D65) | b*(D65) | h | C | L* | a* | b* | dE vs control | dE vs control (media) | dE vs control (S.D.) |
| Control | | 93.38 | −1.87 | 3.30 | 119.54 | 3.79 | 94.47 | −1.92 | 3.10 | | | |
| | | 93.14 | −1.84 | 3.38 | 118.56 | 3.85 | | | | | | |
| | | 94.17 | −2.00 | 2.87 | 124.87 | 3.50 | | | | | | |
| | | 97.18 | −1.97 | 2.83 | 124.84 | 3.45 | | | | | | |
| Labels with $H_2O$ ($H_2S$ ppm) | 92.59 | 71.49 | −0.64 | 10.14 | 93.61 | 10.16 | 72.29 | −0.72 | 10.05 | 24.0673208 | 23.27130874 | 1.32529481 |
| | | 73.85 | −0.78 | 9.90 | 94.50 | 9.93 | | | | 21.7414105 | | |
| | | 71.54 | −0.75 | 10.11 | 94.24 | 10.14 | | | | 24.0051949 | | |
| | 277.78 | 70.95 | −0.64 | 10.27 | 93.57 | 10.29 | 71.13 | −0.63 | 10.36 | 24.6209632 | 24.4733277 | 0.434820524 |
| | | 70.80 | −0.62 | 10.44 | 93.40 | 10.46 | | | | 24.8151079 | | |
| | | 71.65 | −0.63 | 10.37 | 93.48 | 10.39 | | | | 23.9839119 | | |
| | 555.56 | 73.01 | 0.03 | 11.06 | 89.84 | 11.06 | 73.18 | −0.17 | 11.04 | 22.9710259 | 22.79074742 | 0.242321572 |
| | | 73.44 | −0.21 | 10.96 | 91.10 | 10.96 | | | | 22.5152855 | | |
| | | 73.09 | −0.33 | 11.11 | 91.70 | 11.11 | | | | 22.8859309 | | |
| | 833.33 | 73.70 | −0.38 | 10.88 | 92.00 | 10.89 | 73.43 | −0.31 | 11.18 | 22.2321137 | 22.59997957 | 0.323507233 |
| | | 73.24 | −0.26 | 11.36 | 91.31 | 11.36 | | | | 22.8401528 | | |
| | | 73.34 | −0.28 | 11.31 | 91.42 | 11.31 | | | | 22.7276721 | | |
| | 10000 | 71.01 | −0.03 | 10.94 | 90.16 | 10.94 | 71.11 | −0.17 | 10.92 | 24.806661 | 24.69414036 | 0.464025152 |
| | | 70.64 | −0.45 | 10.82 | 92.38 | 10.83 | | | | 25.091558 | | |
| | | 71.69 | −0.03 | 11.00 | 90.16 | 11.00 | | | | 24.1842021 | | |
| Labels without $H_2O$ ($H_2S$ ppm) | 59.65 | 93.88 | −2.01 | 2.81 | 125.58 | 3.45 | 93.89 | −1.94 | 2.82 | 0.65915192 | 0.649811058 | 0.07931115 |
| | | 93.81 | −1.99 | 2.80 | 125.40 | 3.44 | | | | 0.72403816 | | |
| | | 93.97 | −1.83 | 2.84 | 122.80 | 3.38 | | | | 0.5662431 | | |
| | 198.82 | 73.92 | 0.34 | 10.06 | 88.06 | 10.07 | 74.31 | 0.33 | 9.75 | 21.8132662 | 21.35003958 | 0.729374362 |
| | | 75.14 | 0.35 | 9.57 | 87.91 | 9.58 | | | | 20.5092852 | | |
| | | 73.86 | 0.31 | 9.61 | 88.15 | 9.61 | | | | 21.7275673 | | |
| | 397.65 | 72.92 | 0.31 | 10.41 | 88.29 | 10.41 | 72.95 | 0.32 | 10.03 | 22.8643146 | 22.71862635 | 1.060914186 |
| | | 72.03 | 0.41 | 10.36 | 87.73 | 10.37 | | | | 23.6991673 | | |
| | | 73.90 | 0.24 | 9.31 | 88.52 | 9.31 | | | | 21.5923972 | | |
| | 596.47 | 73.43 | 0.47 | 10.05 | 87.32 | 10.06 | 73.59 | 0.47 | 10.31 | 22.2858819 | 22.21817293 | 0.450010522 |
| | | 74.01 | 0.34 | 10.09 | 88.07 | 10.10 | | | | 21.7381446 | | |
| | | 73.34 | 0.61 | 10.80 | 86.77 | 10.82 | | | | 22.6304923 | | |
| | 7952.92 | 71.73 | −0.33 | 10.28 | 91.84 | 10.29 | 71.71 | −0.24 | 10.35 | 23.8986659 | 23.94686845 | 0.850078643 |
| | | 71.01 | 0.02 | 10.97 | 89.90 | 10.97 | | | | 24.8200228 | | |
| | | 72.39 | −0.42 | 9.80 | 92.45 | 9.81 | | | | 23.1219167 | | |

Finally, from the results described above, it was possible to establish a correlation between the indicator gradual colour change measured by Cie Lab coordinates, and the following qualitative and quantitative parameters:

Organoleptic state of the food (not contemplated in the indicator described in the art)
Microbiological state of the food
Concentration of sulphur compounds in the headspace as a consequence of food spoilage.

Figure 7:
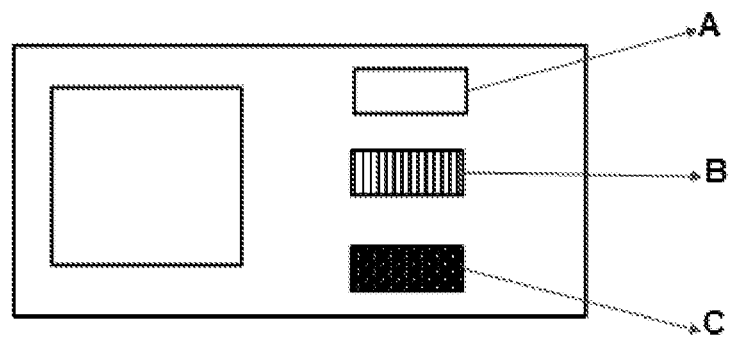
FIG. 7 shows a possible template with which to compare the observed colour change in the label.

Thus, it was possible to build a template with which to compare the observed colour change in the label. An example of that template is shown in FIG. 7, wherein:

A indicates the following parameters:
Microbiollogical quality 2-4 log UFC/g
Sensory quality [9-10] cm
Colour Cie-Lab <0 dE
$[H_2S] \geq 10$ ppm
B indicates the following parameters:
Microbiollogical quality <5 log UFC/g
Sensory quality [6-8] cm
Colour Cie-Lab <25 dE
$[H_2S]$<150 ppm
C indicates the following parameters:
Microbiollogical quality >6 log UFC/g
Sensory quality [2-1] cm
Colour Cie-Lab <40 dE
$[H_2S]$>600 ppm

The invention claimed is:

1. A food freshness indicator ink, which comprises:
   i) a varnish that constitutes between 90-98 weight % of the total ink, said varnish comprising
      i.1) between 5-25 weight % of the total amount of the varnish of at least one film-forming resin or at least one vinylic resin or a mixture thereof;
      i.2) between 10-25 weight % of the amount of the resin of a plasticiser additive; and
      i.3) between 50-75 weight % of the total amount of the varnish of solvents, and
   ii) between 2-10 weight % of the total ink being metallic salts.

2. The ink, according to claim 1, wherein the viscosity of the base ink measured in a Ford Cup No. 4 (FC/4) is 10"-50" at 20° C.

3. The ink, according to claim 1, wherein the resin is a resin derived from cellulose.

4. The ink, according to claim 3, wherein the cellulose derived resin is selected from a wetted nitrocellulose, ethyl cellulose and cellulose aceto-propionate.

5. The ink, according to claim 1, wherein the solvent is selected from ethyl alcohol, ethyl acetate, n-propyl alcohol, n-propyl acetate, ethoxypropanol, methoxypropanol and mixtures thereof.

6. The ink according to claim 1, wherein the solvent is selected from a mixture of ethyl alcohol-ethyl acetate, a mixture of n-propyl alcohol-n-propyl acetate, a mixture of ethyl alcohol-ethyl acetate-methoxypropanol and a mixture of ethyl alcohol-n-propyl acetate-ethoxypropanol.

7. The ink according to claim 1 wherein the plasticizer additive is acetyl tributyl citrate.

8. The ink according to claim 1, wherein the metallic salts are selected from copper and iron salts.

9. The ink according to claim 1 wherein the metallic salts are selected from copper carbonate and iron nitrate.

10. A method for the manufacturing of a food freshness indicator ink, the method comprises:
    a) preparing a varnish by mixing at least one vinylic resin or at least one film forming resin or a mixture thereof, with at least one plasticizer additive that is compatible with the resin, the whole being added to a solvent mixture and stirred until complete solubility, the resin being between 5-25 weight % of the total varnish, the plasticizer additive between 10-25 weight % of the amount of resin and solvents between 50-75 weight % of the total varnish;
    b) preparing a concentrated base ink by adding to the varnish a metal salt, wherein said metal salt is added under slow stirring in the varnish, all the components being stirred subsequently and defining a concentrated base ink, the metal salts being 15-30 weight % and the varnish being between 70-85 weight %, of the total of the ink;
    c) milling the dispersion obtained in step b) in a bead-mill until a dispersion of uniform particle-size distribution smaller than 5µ is obtained;
    d) diluting the concentrated base ink thus obtained in the varnish made in step a), to a metallic salt concentration between 2 and 10% of the total weight of the ink.

11. The method, according to claim 10, wherein the stirring step b) is performed at 1200 rpm for at least 15 minutes.

12. The method, according to claim 1, wherein the milling step is performed in a bead mill with microspheres of zirconium/yttrium oxide for 30 minutes.

13. A label comprising the food freshness indicator ink as defined in claim 1 for detecting gaseous substances comprising sulphur-containing compounds and formed by microbial food spoilage.

14. The label according to claim 13, wherein the label is formed by printing the food freshness indicator ink on a porous substrate or a polymeric matrix.

15. A food package comprising a label as defined in claim 13.

* * * * *